United States Patent
Myoung et al.

(10) Patent No.: US 11,504,409 B2
(45) Date of Patent: Nov. 22, 2022

(54) **COMPOSITION FOR IMPROVING SKIN DAMAGE BY FINE DUST COMPRISING CULTURE OR ITS EXTRACT OF *AUREOBASIDIUM PULLULANS***

(71) Applicant: AMOREPACIFIC CORPORATION, Seoul (KR)

(72) Inventors: Kilsun Myoung, Yongin-si (KR); Hyewon Na, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/765,819

(22) PCT Filed: Nov. 20, 2018

(86) PCT No.: PCT/KR2018/014264
§ 371 (c)(1),
(2) Date: May 20, 2020

(87) PCT Pub. No.: WO2019/098808
PCT Pub. Date: May 23, 2019

(65) Prior Publication Data
US 2020/0384046 A1    Dec. 10, 2020

(30) Foreign Application Priority Data

Nov. 20, 2017    (KR) .......................... 10-2017-0155017

(51) Int. Cl.
| | |
|---|---|
| *A61K 36/06* | (2006.01) |
| *A23L 31/15* | (2016.01) |
| *A61K 8/9728* | (2017.01) |
| *A61Q 19/08* | (2006.01) |

(52) U.S. Cl.
CPC .............. *A61K 36/06* (2013.01); *A23L 31/15* (2016.08); *A61K 8/9728* (2017.08); *A61Q 19/08* (2013.01); *A61K 2236/33* (2013.01); *A61K 2800/40* (2013.01)

(58) Field of Classification Search
None
See application file for complete search history.

(56) References Cited

U.S. PATENT DOCUMENTS

| | | |
|---|---|---|
| 2005/0272694 A1 | 12/2005 | Moriya et al. |
| 2008/0293669 A1 | 11/2008 | Moriya et al. |
| 2010/0068184 A1 | 3/2010 | Moriya et al. |

FOREIGN PATENT DOCUMENTS

| | | |
|---|---|---|
| CN | 101068931 A | 11/2007 |
| JP | 2004-269408 A | 9/2004 |
| JP | 2013-53094 A | 3/2013 |
| JP | 5913988 B2 | 5/2016 |
| KR | 10-2005-0093914 A | 9/2005 |
| KR | 10-2005-0115854 A | 12/2005 |
| KR | 10-2009-0080536 A | 7/2009 |
| KR | 10-2015-0028201 A | 3/2015 |
| KR | 10-2016-0048393 A | 5/2016 |
| KR | 101645476 B1 * | 8/2016 |

OTHER PUBLICATIONS

KR-101645476-B1 translated doc (Year: 2016).*
"Aureobasidium pullulans isolate F3-3-60 18S ribosomal RNA gene, partial sequence; internal transcribed spacer 1, 5.8S ribosomal RNA gene, and internal transcribed spacer 2, complete sequence; and 28S ribosomal RNA gene, partial sequence", NCBI, Genbank, Accession No. KX349501.1 (2016). Available online at: https://www.ncbi.nlm.nih.gov/nucleotide/KX349501.1?report=genbank&log$=nuclal.
Park, Eun-Kyung et al., 'A Study ontheVariation of Skin Moisture, Oil(Sebum), Melaninand Erythemaindex after Application of β-Glucan,' Korean journal of aesthetics and cosmetics society, 2003, vol. 1, No. 3, pp. 83-94.
International Search Report and Written Opinion from International Application No. PCT/KR2018/014264, filed Nov. 20, 2018.
Kyung Hu Kim et al., "Anti-skin-aging benefits of exopolymers from Aureobasidium pullulans SM2001", Journal of Cosmetic Science 65(5): 285-298 (2014).
Kyung Hu Kim et al., "Inhibition of UVB-induced Skin Damage by Exopolymers from Aureobasidium pullulans SM-2001 in Hairless Mice", Basic & Clinical Pharmacology & Toxicology 116(2): 73-86 (2015).
Office Action for Chinese Patent Application No. 201880075172.1 (dated Jul. 20, 2021).
Seo-Yeon Park et al., "Air Pollution, Autophagy, and Skin Aging: Impact of Particulate Matter (PM10) on Human Dermal Fibroblasts", International Journal of Molecular Sciences 19, 2727: 1-15 (2018).

(Continued)

*Primary Examiner* — Terry A McKelvey
*Assistant Examiner* — Jacob A Boeckelman
(74) *Attorney, Agent, or Firm* — Merchant & Gould P.C.

(57) ABSTRACT

Disclosed in the present disclosure is a composition for improving skin damage caused by fine dust, which contains an *Aureobasidium pullulans* strain; a lysate thereof; a culture thereof; or an extract of the strain, the lysate or the culture as an active ingredient, and the composition has an effect of promoting the expression of keratinocyte differentiation markers and granular layer tight junction markers, thereby enhancing the skin barrier function and having skin-moisturizing, anti-aging and wrinkle-suppressing effects, and, thus, has an excellent effect in terms of improving skin damage caused by fine dust.

10 Claims, 3 Drawing Sheets

Specification includes a Sequence Listing.

(56) References Cited

OTHER PUBLICATIONS

Poonam Puri et al., "Effects of air pollution on the skin: A review", Review Article, Indian Journal of Dermatology, Venereology, and Leprology 83(4): 415-423 (2017).

Natalia D. Magnani et al., "Skin Damage Mechanisms Related to Airborne Particulate Matter Exposure", Toxicological Sciences 149(1): 227-236 (2016).

* cited by examiner

SEQUENCE LISTING

```
<160> NUMBER OF SEQ ID NOS: 7

<210> SEQ ID NO 1
<211> LENGTH: 574
<212> TYPE: DNA
<213> ORGANISM: Artificial Sequence
<220> FEATURE:
<223> OTHER INFORMATION: 18S rRNA

<400> SEQUENCE: 1
ggggactgcg gaggatcatt aagagtaagg gtgctcagcg cccgacctcc aaccctttgt      60
tgttaaaact accttgttgc tttggcggga ccgctcggtc tcgagccgct ggggattcgt     120
cccaggcgag cgcccgccag agttaaacca aactcttgtt attaaaccgg tcgtctgagt     180
taaaattttg aataaatcaa aactttcaac aacggatctc ttggttctcg catcgatgaa     240
```

| | | |
|---|---|---|
| gaacgcagcg aaatgcgata agtaatgtga attgcagaat tcagtgaatc atcgaatctt | 300 | |
| tgaacgcaca ttgcgcccct tggtattccg aggggcatgc ctgttcgagc gtcattacac | 360 | |
| cactcaagct atgcttggta ttgggtgccg tccttagttg ggcgcgcctt aaagacctcg | 420 | |
| gcgaggcctc accggcttta ggcgtattag aatttattcg aacgtctgtc aaaggagagg | 480 | |
| acttctgccg actgaaacct tttattttc taggttgacc tcggatcagg tagggatacc | 540 | |
| cgctgaactt aagcatatca ataaggcgga ggaa | 574 | |

<210> SEQ ID NO 2
<211> LENGTH: 19
<212> TYPE: DNA
<213> ORGANISM: Artificial Sequence
<220> FEATURE:
<223> OTHER INFORMATION: ITS1

<400> SEQUENCE: 2
tccgtaggtg aacctgcgg    19

<210> SEQ ID NO 3
<211> LENGTH: 20
<212> TYPE: DNA
<213> ORGANISM: Artificial Sequence
<220> FEATURE:
<223> OTHER INFORMATION: ITS4

<400> SEQUENCE: 3
tcctccgctt attgatatgc    20

<210> SEQ ID NO 4
<211> LENGTH: 25
<212> TYPE: DNA
<213> ORGANISM: Artificial Sequence
<220> FEATURE:
<223> OTHER INFORMATION: Ker1F

<400> SEQUENCE: 4
aggtcgattt gtcccagcct taccg    25

<210> SEQ ID NO 5
<211> LENGTH: 25
<212> TYPE: DNA
<213> ORGANISM: Artificial Sequence
<220> FEATURE:
<223> OTHER INFORMATION: Ker1R

<400> SEQUENCE: 5
atgtcatgtg ggtggtggtc actgc    25

<210> SEQ ID NO 6
<211> LENGTH: 23
<212> TYPE: DNA
<213> ORGANISM: Artificial Sequence
<220> FEATURE:
<223> OTHER INFORMATION: Claudin-4 F

<400> SEQUENCE: 6
gtgtaaggtg ctaccgctga ttc    23

<210> SEQ ID NO 7
<211> LENGTH: 20
<212> TYPE: DNA
<213> ORGANISM: Artificial Sequence
<220> FEATURE:
<223> OTHER INFORMATION: Claudin-4 R

```
<400> SEQUENCE: 7
agggccattc tggagtcaca                                              20
```

COMPOSITION FOR IMPROVING SKIN DAMAGE BY FINE DUST COMPRISING CULTURE OR ITS EXTRACT OF *AUREOBASIDIUM PULLULANS*

This application is a National Stage Application of International Application No. PCT/KR2018/014264, filed Nov. 20, 2018, which claims benefit of Serial No. 10-2017-0155017, filed Nov. 20, 2017 in the Republic of Korea. Both of the aforementioned applications are incorporated herein by reference. To the extent appropriate, a claim of priority is made to each of the above disclosed applications.

TECHNICAL FIELD

Disclosed in the present disclosure is a composition for improving skin damage caused by fine dust, which comprises an *Aureobasidium pullulans* strain, a lysate thereof, a culture thereof, or an extract of the strain, the lysate or the culture as an active ingredient.

BACKGROUND ART

Recently, with increased avoidance of chemicals and insect- and animal-based substances, the demand on environment-friendly biomaterials is increasing. Microbial resources are renewable unlike petroleum, water, etc., and are classified as sustainable resources and are highly applicable to researches and industries since the intrinsic characteristics of microorganisms that adapt to various environments are utilized.

Meanwhile, skin serves as a barrier between the body and the environment. It is known that the barrier function is decreased by frequent exposure to fine dust. In particular, because the fine dust is 20 times smaller than hair follicles, it can penetrate easily into the skin. Therefore, fine dust can cause premature aging, water insufficiency and increase fine wrinkles and wrinkles in the short term, and can cause severe diseases such as skin cancer in the long term as the skin's function of protecting the body from environmental factors is lost due to irreversible skin damage.

*Aureobasidium pullulans*, commonly known as black yeast, is one of the microorganisms found in soil or air and exhibits excellent environmental adaptation. *Aureobasidium pullulans* can survive and grow even in harsh environments of low humidity, high temperature, intense solar radiation, and even radionuclides. It is known to protect itself from UV or organic free radicals by producing the melanin pigment like human skin and to protect itself from external environment by producing ß-glucans such as pullulan, etc. around it (N. A. Yurlova et al. 2008. *Studies in Microbiology* 61: 39-49). Although the anti-oxidative effect, skin-protecting effect against atopy, etc. are known for pullulan, nothing is known about the effect of protecting skin from fine dust.

DISCLOSURE

Technical Problem

In an aspect, the present disclosure is directed to providing a new use of an *Aureobasidium pullulans* strain.

In another aspect, the present disclosure is directed to providing an *Aureobasidium pullulans* GJW strain which has a superior effect in improving skin damage caused by fine dust.

Technical Solution

In an aspect, the present disclosure provides a composition for improving skin damage caused by fine dust, which comprises an *Aureobasidium pullulans* strain; a lysate thereof; a culture thereof; or an extract of the strain, the lysate or the culture as an active ingredient.

In another aspect, the present disclosure provides an *Aureobasidium pullulans* GJW strain which has a superior effect in improving skin damage caused by fine dust.

Advantageous Effects

In an aspect, an *Aureobasidium pullulans* strain; a lysate thereof; a culture thereof; or an extract of the strain, the lysate or the culture of the present disclosure has an effect of promoting the expression of keratinocyte differentiation markers and granular layer tight junction markers, thereby enhancing the skin barrier function and having skin-moisturizing, anti-aging and wrinkle-improving effects, and, thus, has an excellent effect in terms of improving skin damage caused by fine dust.

BEST MODE

Figure 1:
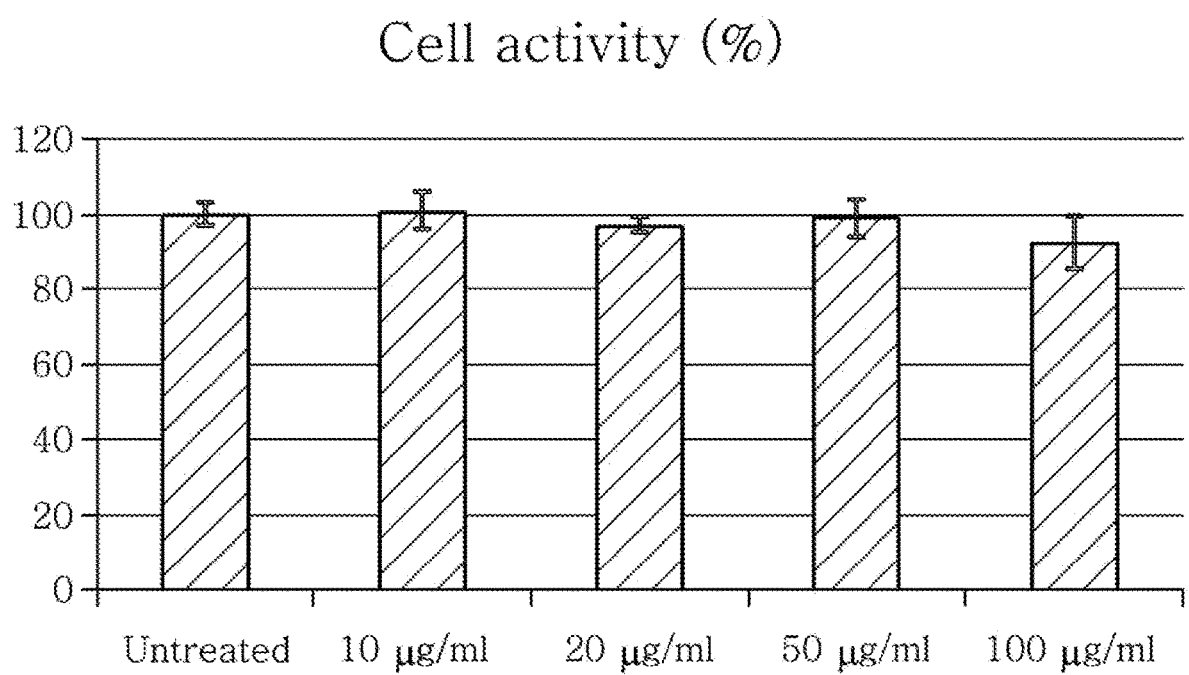
FIG. 1 shows the skin cell stability of an *Aureobasidium pullulans* GJW strain.

Hereinafter, the present disclosure is described in detail.

In an aspect, the present disclosure provides a composition for improving skin damage caused by fine dust, which comprises an *Aureobasidium pullulans* strain; a lysate thereof; a culture thereof; or an extract of the strain, the lysate or the culture as an active ingredient.

The *Aureobasidium pullulans* strain of the present disclosure may be an *Aureobasidium pullulans* GJW strain having an accession number of KCCM12142P, and may specifically have 18S rRNA represented by SEQ ID NO 1. The strain may be prepared as follows. After culturing and centrifuging the culture, followed by washing with sterilized physiological saline, suspending in a solvent, e.g., sterilized milk and freezing-drying, it may be prepared into freeze-dried powder and used.

The lysate of the strain may be a product obtained by lysing the strain itself either chemically or by applying physical force.

The culture of the strain may refer to a substance containing some or all substances included in the culture medium in which the strain was cultured, regardless of the type of the culture. For example, it may refer to a substance including a metabolite or a secreted product resulting from the culturing of the strain, or a lysate thereof, and the strain itself may also be included in the culture. In an exemplary embodiment of the present disclosure, the culture may be one cultured in a culture medium comprising potato extract and dextrose.

The extract may refer to a product obtained by extracting the strain itself, a lysate of the strain, a culture of the strain or a mixture thereof, regardless of extraction method, extraction solvent, extracted ingredients or type of the extract. The extract is used in a broad concept, including any substance that can be obtained through processing or treating by another method after the extraction. Specifically, the extract may be an ethanol fraction.

The *Aureobasidium pullulans* strain; a lysate thereof; a culture thereof; or an extract of the strain, the lysate or the culture may be contained in the composition of the present disclosure in an amount of 0.001-30 wt % based on the total weight of the composition. Specifically, it may be contained in an amount of 0.001 wt % or more, 0.01 wt % or more, 0.1 wt % or more, 0.5 wt % or more, 1 wt % or more, 1.5 wt % or more or 2 wt % or more, and 30 wt % or less, 25 wt % or less, 20 wt % or less, 15 wt % or less, 10 wt % or less or 5 wt % or less, based on the total weight of the composition.

In the present disclosure, the fine dust refers to very small particulate matter invisible to human eyes, which floats or flutters in the atmosphere for a long time. It may refer to dust with a particle diameter of 10 μm or smaller. In particular, the particulate matter having a particle diameter of 2.5 μm or smaller is called ultrafine dust. In the present disclosure, the fine dust includes ultrafine dust, too. The particle diameter may mean the average value of the diameter of the dust particles. The dust includes materials derived from nature such as sand, soil and pollen and materials derived from industrial processes such as carbon, carbon combustion products, metal salts and heavy metals. In general, the fine dust is composed of 22% of organic carbon compounds, 8% of carbon, 22% of nitrates, 15% of sulfates, 15% of soil components and 18% of other components.

In the present disclosure, the skin damage caused by fine dust refers to skin damage resulting from stimulation by fine dust. The skin damage is used in a broad concept, including the decline or weakening of skin function. Specifically, it may comprise decline in skin barrier (stratum corneum) function, decline in skin-moisturizing ability, or formation of skin wrinkles, etc. The skin barrier is composed of dead keratinocytes (corneocytes) and intercellular lipids, and plays a critical role in skin health as a skin-protecting membrane by protecting the skin from external stimulation and preventing evaporation of water from the skin. Accordingly, the decline in skin barrier function may lead to skin dryness, accelerated aging and increased wrinkle formation. In the present disclosure, the improvement of skin damage caused by fine dust may be enhancement of the skin barrier function, miniaturization of the skin, anti-aging or improvement of wrinkles.

The composition of the present disclosure may increase the expression of keratin 1 or claudin 4. The keratin 1 is one of keratinocyte differentiation markers. Keratin is one of a family of intermediate fibrous proteins forming intermediate filaments in animal cells. In particular, it is an important structural protein that forms keratin filaments in epimermal cells such as the skin. If the expression level of keratin 1 is high, it can be determined that the differentiation of skin cells, specifically keratinocytes, occurs actively. The claudin 4 is a granular layer tight junction marker, and is one of the genes that encode the claudin protein, which is one of tight junction proteins. The granular layer is one of layers existing in the mammalian epidermis (cornified stratified squamous epithelium). The tight junction joins together adjacent cells. It fills gaps between adjacent cells, regulates transport of small substances between cells, controls permeation of substances between cells, maintains cell polarity, and plays an important role in skin barrier function. The composition of the present disclosure for improving skin damage caused by fine dust has an effect of enhancing skin barrier function and skin-moisturizing, anti-aging and wrinkle-improving effects by promoting the differentiation of keratinocytes and promoting the expression of granular layer tight junction genes.

According to an exemplary embodiment of the present disclosure, the expression level of the keratinocyte differentiation marker keratin 1 and the granular layer tight junction marker claudin 4 in keratinocytes treated with a fine dust dispersion (control group) was decreased to about 40% as compared to a group not treated with the fine dust dispersion. Due to decreased differentiation of keratinocyte differentiation and granular layer tight junction expression caused by fine dust, skin damage occurred, including decline in skin barrier function, increased skin dryness and skin aging, accelerated wrinkle formation, etc. (Experimental Examples 2 and 3, FIGS. 2 and 3). In addition, when the keratinocytes treated with the fine dust dispersion were treated with a culture extract of the *Aureobasidium pullulans* strain of the present disclosure, the keratin 1 expression level and the claudin 4 expression level were increased by about 50%, respectively, at a higher level than when treated with pullulan. Accordingly, it was confirmed that the culture extract of the *Aureobasidium pullulans* strain of the present disclosure has skin-moisturizing, anti-aging and wrinkle-improving effects by exhibiting superior effect of promoting keratinocyte differentiation and enhancing the skin barrier function damaged by fine dust (Experimental Examples 2 and 3, FIGS. 2 and 3).

In another aspect, the present disclosure may relate to a method for improving skin damage, which comprises administering a composition comprising an *Aureobasidium pullulans* strain; a lysate thereof; a culture thereof; or an extract of the strain, the lysate or the culture to a subject in need of improvement of skin damage caused by fine dust. In an aspect of the present disclosure, the administration in the method may be performed according to the administration method and administration dosage described in the present disclosure.

In another aspect, the present disclosure may relate to a method for preventing, improving or treating a skin disease induced by skin damage caused by fine dust, which comprises administering a composition comprising an *Aureobasidium pullulans* strain; a lysate thereof; a culture thereof; or an extract of the strain, the lysate or the culture to a subject in need of prevention, improvement or treatment of a skin disease induced by skin damage caused by fine dust. In an aspect of the present disclosure, the administration in the method may be performed according to the administration method and administration dosage described in the present disclosure.

In another aspect, the present disclosure may relate to a use of an *Aureobasidium pullulans* strain; a lysate thereof; a culture thereof; or an extract of the strain, the lysate or the culture for preparation of a pharmaceutical composition for preventing, improving or treating a skin disease induced by skin damage caused by fine dust.

In another aspect, the present disclosure may relate to a use of an *Aureobasidium pullulans* strain; a lysate thereof; a culture thereof; or an extract of the strain, the lysate or the culture for preparation of a cosmetic composition for improving a skin damage caused by fine dust.

In another aspect, the present disclosure may relate to a use of an *Aureobasidium pullulans* strain; a lysate thereof; a culture thereof; or an extract of the strain, the lysate or the culture for preparation of a food composition for improving skin damage caused by fine dust.

In another aspect, the present disclosure may relate to a use of an *Aureobasidium pullulans* strain; a lysate thereof; a culture thereof; or an extract of the strain, the lysate or the culture for improvement of skin damage caused by fine dust.

In another aspect, the present disclosure may relate to a use of an *Aureobasidium pullulans* strain; a lysate thereof; a culture thereof; or an extract of the strain, the lysate or the culture for improving skin damage caused by fine dust.

In these aspects, the composition may be a pharmaceutical composition, a cosmetic composition or a food composition.

The pharmaceutical composition may be prepared into a formulation for oral administration or parenteral administration in the form of solid, semisolid or liquid by adding a commonly used inorganic or organic carrier to the composition containing the active ingredient.

The formulation for oral administration may be a tablet, a pill, a granule, a soft or hard capsule, a powder, a fine granule, an emulsion, a syrup, a pellet, etc. And, the formulation for parenteral administration may be an injection, a medicinal drop, an ointment, a lotion, a spray, a suspension, an emulsion, a suppository, etc. The composition of the present disclosure may be easily prepared into such a formulation according to common methods, and a surfactant, an excipient, a colorant, a fragrance, a preservative, a stabilizer, a buffer, a suspending agent or other commonly used adjuvant may be used appropriately.

Since the pharmaceutical composition according to the present disclosure exhibits superior effect of improving skin damage caused by fine dust, it can be usefully used to treat or prevent a skin disease induced by skin damage caused by fine dust. The skin disease induced by skin damage caused by fine dust may be atopic dermatitis, xeroderma, psoriasis, ichthyosis, acne, etc., although not being limited thereto.

The pharmaceutical composition may be administered orally, parenterally, rectally, topically, transdermally, intravenously, intramuscularly, intraperitoneally, subcutaneously, etc.

The administration dosage of the active agent will vary depending on the age, sex and body weight of a subject to be treated, the particular disease or pathological condition be treated, the severity of the disease or pathological condition, administration route and the discretion by a diagnoser. The determination of the administration dosage based on these factors are within the level of those skilled in the art. The administration dosage is generally 0.001-2000 mg/kg/day, specifically 0.5-1500 mg/kg/day.

The cosmetic composition may be provided in the form of all topically applicable formulations. For example, it may be provided as a formulation in the form of a solution, an oil-in-water emulsion, a water-in-oil emulsion, a suspension, a solid, a gel, a powder, a paste, a foam or an aerosol composition. Compositions of these formulations may be prepared according to common methods in the art.

Specifically, the cosmetic composition may further contain other ingredients, in addition to substances, that may provide a synergistic effect within a range not negatively affecting the main effect. The cosmetic composition according to the present disclosure may contain one or more substance selected from a group consisting of a vitamin, a polypeptide, a polysaccharide and a sphingolipid. In addition, the cosmetic composition according to the present disclosure may contain a humectant, an emollient, a surfactant, a UV absorbent, an antiseptic, a sterilizer, an antioxidant, a pH control agent, an organic or inorganic pigment, a fragrance, a cooling agent or an antiperspirant. The mixing amount of these ingredients may be selected easily by those skilled in the art in a range not negatively affecting the purpose and effect of the present disclosure. The mixing amount may be 0.001-5 wt %, specifically 0.01-3 wt %, based on the total weight of the composition.

The pharmaceutical composition or the cosmetic composition may be a composition for external application to skin, e.g., a cream or an ointment.

The food composition may be a health food composition, and may be a fermented food composition requiring fermentation, e.g., tea, dairy products, kimchi and brewed foods. The formulation of the food composition is not particularly limited. For example, it may be formulated as a tablet, a pill, a soft or hard capsule, a granule, a drink, a caramel, a diet bar, a tea bag, etc. The food composition of each formulation may contain, in addition to the active ingredient, ingredients commonly used in the art that may be selected without difficulty by those skilled in the art depending on the particular formulation or purpose of use. A synergistic effect may occur when the additional ingredients are used together. The determination of the administration dosage of the active ingredient is within the level of those skilled in the art and may vary depending on various conditions such as the age and health condition of a subject to be treated, the presence of complications, etc.

Hereinafter, the present disclosure will be described in detail through the following examples and experimental examples. However, the following examples and experimental examples are for illustrative purposes only to help understand the present disclosure and the scope of the present disclosure is not limited by them.

[Example 1] Isolation and Identification of Strain

*Aureobasidium pullulans* was isolated from green bean ferns harvested in the Gotjawal Forest on Jeju Island. The isolation was conducted as follows.

First, the harvested green bean ferns were washed once with sterile distilled water to remove impurities, immersed in phosphate-buffered saline (PBS) corresponding to 10 times based on weight, and then incubated at a speed of 250 rpm for 1 hour. Then, after diluting the PBS solution to physiological saline 10-fold and 100-fold, it was inoculated to PDA (4 g/L potato extract, 20 g/L dextrose, 15 g/L agar). Then, the inoculated medium was incubated at 25-30° C. for 2-7 days, and a single strain was isolated finally by subculturing strain for 2-4 passages that forms a colony.

The isolated strain was identified through 18S rRNA base sequencing using an ITS1 primer and an ITS4 primer described in Table 1 below. As a result of Gene Bank search of the sequenced base sequence, the isolated strain was confirmed to have 94% similarity to the 18S rRNA base sequence of *Aureobasidium pullulans* F3-3-60 and was named as *Aureobasidium pullulans* GJW. The strain was deposited on Oct. 31, 2017 in the Korean Culture Center of Microorganisms, under the provisions of the Budapest Treaty, and was given the accession number KCCM12142P.

TABLE 1

| | | |
|---|---|---|
| SEQ ID NO 2 | ITS1 | 5'-TCC GTA GGT GAA CCT GCG G-3' |
| SEQ ID NO 3 | ITS4 | 5'-TCC TCC GCT TAT TGA TAT GC-3' |

[Example 2] Preparation of Culture and Extract of *Aureobasidium pullulans* GJW

The *Aureobasidium pullulans* (*A. pullulans*) GJW strain was inoculated to a culture medium (4 g/L potato extract, 20 g/L dextrose) and a culture was obtained by culturing the same at 30° C. and 120 rpm for 5 days.

The obtained culture of the *Aureobasidium pullulans* (*A. pullulans*) GJW strain was added to ethanol of the same volume and an ethanol fraction was obtained by conducting reaction and remaining stationary at 4° C. for 1 day. Then, a culture extract was obtained by conducting centrifugation and freeze-drying.

[Example 3] Collection and Extraction of Fine Dust

Fine dust was collected using a low-volume air sampler (Sensidyne, Gillian, Fla., USA). Sampling was conducted for about 24 hours while replacing a filter and a denuder of a filter pack around 10 a.m. on the day when sampling was made. Fine dust was collected every day from Feb. 1, 2014 until Feb. 28, 2014 in an area downwind from Seoul, Korea (the rooftop of a six-story building of Dormitory of the Center for Foreign Studies at Hankuk University of Foreign Sutdies located in Cheoin-gu, Yongin-si, Gyeonggi-do). The measurement time was recorded by checking the time of the timer when a vacuum pump was turned off, which the timer was started while a vacuum pump was turned on. Sampling rate, which was set to 16.7 L/min, was measured when the sampling was started and finished using a flow meter (Model 4143, TSI Inc.). A Teflon filter loaded into the filter pack was weighed before and after the sampling. Before weighing the Teflon filter, it was settled for 24 hours in a desiccator (Nikko, Japan) of 40% relative humidity. The weight was measured twice using an electronic balance (DVG215CD, Ohaus) to the five digits to the right of the decimal point and then recorded as the average value. Also, after the sampling, the filter was weighed twice after weighing for 24 hours in the desiccator before measuring the weight. Mass concentration was calculated by comparing with the weight measured before the sampling. The fine dust was extracted as follows. The Teflon filter was soaked in 1 mL of ethanol. After 14 mL of DW was added and the lid was closed while the aerosol capturing surface of the filter was in contact with the water level, and then extraction of fine dust was conducted for 30 minutes by ultrasonic waves with ultrasonic cleaner. After completely removing water from the filter in a desiccator for 48 hours to minimize error, the weight of the filter before and after the extraction was measured using a high-precision balance (Mettler Toledo Company) which can measure up to 0.1 mg.

[Example 4] Culturing of Keratinocytes

Keratinocytes (human normal epidermal keratinocytes) purchased from Lonza, Inc. (Walkersville, Md., USA) were subcultured and then cultured in a $CO_2$ incubator under the condition of 37° C. and 5% $CO_2$. 500 mL of a KBM-2 (KBMTM-2, CC-3103) medium containing BPE (bovine pituitary extract), human epidermal growth factor (hEGF), insulin, hydrocortisone, gentamycin sulfate, epinephrine and transferrin was used. During the culturing, the maximum confluency of about 90% was maintained, and then was subcultured.

[Example 5] Treatment of Keratinocytes with Fine Dust and Culture Extract of *Aureobasidium pullulans* Strain The keratinocytes cultured under the cell culture condition in culturing of keratinocytes of Example 4 treated with 50 µg/mL of the fine dust obtained in Example 3 using a 6-well plate, at $3 \times 10^5$ cells/well, and cultured for 24 hours were used as a control group (hereinafter, an 'untreated group' refers to keratinocytes not treated with the fine dust dispersion). Also, in the same manner, the cells were treated 50 µg/mL of the fine dust and 50 µg/mL of the *Aureobasidium pullulans* GJW extract of Example 2, or with 50 µg/mL of the fine dust and 50 µg/mL of pullulan, which is known to be produced by *Aureobasidium pullulans*, as a comparative example, and cultured for 24 hours.

[Experimental Example 1] Confirmation of Skin Cell Safety of Culture Extract of *Aureobasidium pullulans* Strain Experiment was conducted as follows to confirm the culture extract of the *Aureobasidium pullulans* strain obtained in Example 2 is safe for skin cells.

After dissolving the culture extract of the *Aureobasidium pullulans* strain obtained in Example 2 in purified water (DW) and treating keratinocytes with the extract, the effect on the activity of the cells was investigated. After seeding 100 µL of the skin cells onto each 96-well cell culture plate at a concentration of $2 \times 10^5$ cells/mL and culturing for 24 hours, followed by treating with the culture extract of the *Aureobasidium pullulans* strain at concentrations of 10 µg/mL, 20 µg/mL, 50 µg/mL and 100 µg/mL, respectively, the cells were cultured further for 24 hours. The experiment was repeated 3 times for the respective concentrations. The cell activity was compared by MTT assay and was represented relative to the activity of the untreated group as 100%.

As a result, the culture extract of the *Aureobasidium pullulans* strain was confirmed to be safe for the skin cells since they had no effect on the growth of the skin cells (see FIG. 1).

[Experimental Example 2] Keratinocyte Differentiation-Promoting Effect of Culture Extract of the *Aureobasidium pullulans* Strain Experiment was conducted as follows to confirm the keratinocyte differentiation-promoting effect of the culture extract of the *Aureobasidium pullulans* strain obtained in Example 2.

After removing the culture from each of the untreated group, the keratinocytes treated with the fine dust but with neither the culture extract of the *Aureobasidium pullulans* strain nor pullulan (hereinafter, 'control group'), the keratinocytes treated with the fine dust and the culture extract of the *Aureobasidium pullulans* strain ('*A. pullulans* culture extract' in FIG. 2) and the keratinocytes treated with the fine dust dispersion and pullulan of Example 5 ('pullulan' in FIG. 2) and washing the cells with 2 mL of phosphate-buffered saline (PBS), RNA was isolated from the cells using a Trizol reagent (Invitrogen, Carlsbad, Calif., USA). Then, after purifying the isolated RNA once again using the QIAGEN RNeasy kit (QIAGEN, Valencia, Calif.), the quality of the RNA was investigated using the Agilent 2100 BioAnalyzer (Agilent Technologies, Santa Clara, Calif., USA). Then, cDNA was synthesized from the RNA using the Superscript Reverse Transcriptase (RT) kit (Invitrogen, Carlsbad, Calif.).

Figure 2:
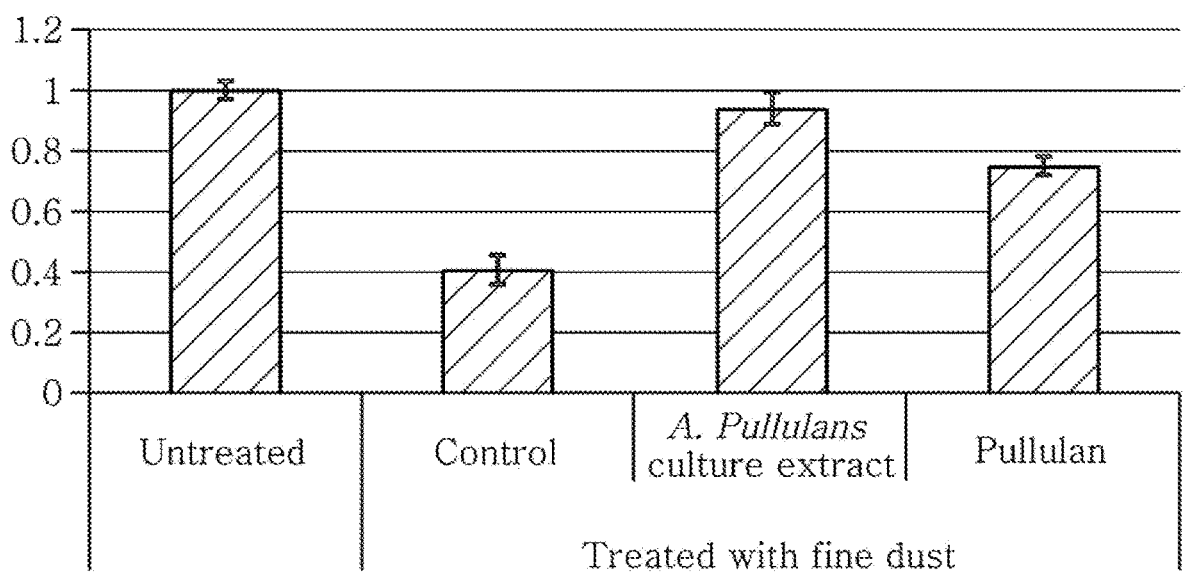
FIG. 2 shows the relative expression level of keratin 1 in keratinocytes treated with a culture extract of an *Aureobasidium pullulans* GJW strain.

Subsequently, the expression level of keratin 1 was analyzed quantitatively through real-time reverse transcription polymerase chain reaction (Q-RT-PCR) using the primers described in Table 2. The change in the gene expression pattern of the cells was evaluated by real-time PCR using the TaqMan gene expression assay kit (Applied Biosystems, Foster City, Calif.). The result is shown in FIG. 2. The relative mRNA expression level shown in FIG. 2 represents the mRNA expression level of keratin 1 with respect to the keratin 1 mRNA expression level of the untreated group as 1. The Q-RT-PCR and real-time PCR were conducted in accordance with the standard protocols of Life Technologies, specifically, at 95° C. for 20 seconds, followed by 40 cycles of 95° C. for 3 seconds and 60° C. for 30 seconds.

TABLE 2

| SEQ ID NO 4 | Ker1F | 5-AGG TCG ATT TGT CCC AGC TTT ACC G-3' |
|---|---|---|
| SEQ ID NO 5 | Ker1R | 5-ATG TCA TGT GGG TGG TGG TCA CTG C-3' |

As seen from FIG. 2, when the keratinocytes were treated with the fine dust dispersion, the expression level of keratin 1 was decreased to about 40%, which suggests that the fine dust causes skin damage by inhibiting the differentiation of keratinocytes. When the keratinocytes damaged by the fine dust were treated with the culture extract of the *Aureobasidium pullulans* strain prepared in Example 2, the expression level of keratin 1 was increased by 50% or higher, which is that the expression is promoted more than when treated with pullulan. Accordingly, it was confirmed that the culture extract of the *Aureobasidium pullulans* strain of the present disclosure exhibits superior keratinocyte differentiation-promoting effect and skin-moisturizing, anti-aging and wrinkle-improving effects by enhancing the skin barrier function damaged by fine dust.

[Experimental Example 3] Granular Layer Tight Junction Marker Expression-Promoting Effect of Culture Extract of the *Aureobasidium pullulans* Strain Experiment was conducted as follows to confirm the granular layer tight junction marker expression-promoting effect of the culture extract of the *Aureobasidium pullulans* strain obtained in Example 2.

Figure 3:
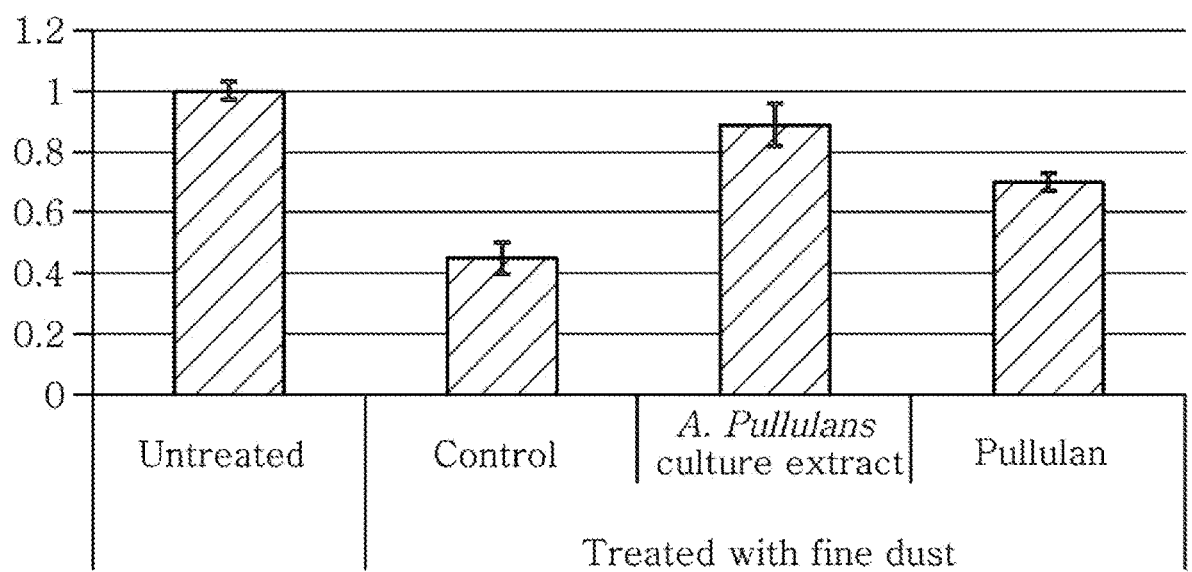
FIG. 3 shows the relative expression level of claudin 4 in keratinocytes treated with a culture extract of an *Aureobasidium pullulans* GJW strain.

After isolating RNA from each of cells of the untreated group, the keratinocytes treated with the fine dust but with neither the culture extract of the *Aureobasidium pullulans* strain nor pullulan (hereinafter, 'control group'), the keratinocytes treated with the fine dust and the culture extract of the *Aureobasidium pullulans* strain ('*A. pullulans* culture extract' in FIG. 3) and the keratinocytes treated with the fine dust dispersion and pullulan ('pullulan' in FIG. 3) in the same manner as in Experimental Example 2, the mRNA expression level of claudin 4 was measured. The result is shown in FIG. 3. The primer sequences used are described in Table 3. The relative mRNA expression level shown in FIG. 3 represents the mRNA expression level of claudin 4 with respect to the claudin 4 mRNA expression level of the untreated group as 1.

TABLE 3

| SEQ ID NO 6 | Claudin-4F | 5'-GTG TAA GGT GCT ACC GCT GAT TC-3' |
|---|---|---|
| SEQ ID NO 7 | Claudin-4R | 5'-AGG GCC ATT CTG GAG TCA CA-3' |

As seen from FIG. 3, when the keratinocytes were treated with the fine dust dispersion, the expression level of claudin 4, which is one of the constituents of tight junction which is the granular layer barrier, was decreased to about 40%, which suggests that the fine dust causes skin damage by inhibiting the expression of the granular layer tight junction marker. When the keratinocytes damaged by the fine dust were treated with the culture extract of the *Aureobasidium pullulans* strain prepared in Example 2, the expression level of claudin 4 was increased by 50% or higher, more than when treated with pullulan. Accordingly, it was confirmed that the culture extract of the *Aureobasidium pullulans* strain of the present disclosure exhibits superior effect of promoting granular layer tight junction marker expression and skin-moisturizing, anti-aging and wrinkle-improving effects by enhancing the skin barrier function damaged by fine dust.

Hereinafter, the present disclosure will be described in detail through formulation examples. However, it can be applied to various other formulations and the following examples are for illustrative purposes only and the scope of the present disclosure is not limited by the examples.

[Formulation Example 1] Softening Lotion

A softening lotion was prepared according to a common method by mixing 0.01 wt % of the *Aureobasidium pullulans* culture of Example 2, 3 wt % of glycerin, 2 wt % of butylene glycol, 2 wt % of propylene glycol, 0.1 wt % of a carboxyvinyl polymer, 10 wt % of ethanol, 0.1 wt % of triethanolamine, an antiseptic as balance, a trace amount of a colorant, a trace amount of a fragrance and a trace amount of purified water.

[Formulation Example 2] Nourishing Lotion

A nourishing lotion was prepared according to a common method by mixing 0.01 wt % of the *Aureobasidium pullulans* culture of Example 2, 4 wt % of beeswax, 1.5 wt % of polysorbate 60, 0.5 wt % of sorbitan sesquioleate, 5 wt % of liquid paraffin, 5 wt % of squalane, 5 wt % of caprylic/capric triglyceride, 3 wt % of glycerin, 3 wt % of butylene glycol, 3 wt % of propylene glycol, 0.1 wt % of a carboxyvinyl polymer, 0.2 wt % of triethanolamine, an antiseptic as balance, a trace amount of a colorant, a trace amount of a fragrance and a trace amount of purified water.

[Formulation Example 3] Nourishing Cream

A nourishing cream was prepared according to a common method by mixing 0.01 wt % of the *Aureobasidium pullulans* culture of Example 2, 10 wt % of beeswax, 1.5 wt % of polysorbate 60, 0.5 wt % of sorbitan sesquioleate, 10 wt % of liquid paraffin, 5 wt % of squalane, 5 wt % of caprylic/capric triglyceride, 5 wt % of glycerin, 3 wt % of butylene glycol, 3 wt % of propylene glycol, 0.2 wt % of triethanolamine, an antiseptic as balance, a trace amount of a colorant, a trace amount of fragrance and a trace amount of purified water.

[Formulation Example 4] Pack

A pack was prepared according to a common method by mixing 0.01 wt % of the *Aureobasidium pullulans* culture of Example 2, 13 wt % of polyvinyl alcohol, 0.2 wt % of sodium carboxymethyl cellulose, 0.1 wt % of allantoin, 5 wt % of ethanol, 0.3 wt % of nonyl phenyl ether, an antiseptic as balance, a trace amount of a colorant, a trace amount of fragrance and a trace amount of purified water.

[Formulation Example 5] Medication for Topical Administration (Patch)

A medication for topical administration (patch) was prepared according to a common method with the composition described in Table 4.

TABLE 4

| Ingredients | Contents (wt %) |
|---|---|
| *Aureobasidium pullulans* culture of Example 2 | 2.0 |
| Beta-1,3-glucan | 3.0 |
| Diethylamine | 0.7 |
| Sodium sulfite | 0.1 |
| Polyoxyethylene lauryl ether (E.O = 9) | 1.0 |
| Polyhydroxyethylene cetyl stearyl ether (Cetomacrogol 1000) | 1.0 |
| Viscous paraffin oil | 2.5 |
| Caprylic/capric acid ester (Cetiol LC) | 2.5 |
| Polyethylene glycol 400 | 3.0 |
| Polyacrylic acid (Carbopol 934P) | 1.0 |
| Purified water | balance |
| Total | 100 |

[Formulation Example 6] Powder

A powder was prepared by mixing 2 g of the *Aureobasidium pullulans* culture of Example 2 and 1 g of lactose and filling the same in an airtight pouch.

[Formulation Example 7] Tablet

A tablet was prepared according to a common method after mixing 100 mg of the *Aureobasidium pullulans* culture of Example 2, 100 mg of corn starch, 100 mg of lactose and 2 mg of magnesium stearate.

[Formulation Example 8] Capsule

A capsule was prepared according to a common method by mixing 100 mg of the *Aureobasidium pullulans* culture of Example 2, 100 mg of corn starch, 100 mg of lactose and 2 mg of magnesium stearate and then filling the mixture in a gelatin capsule.

[Formulation Example 9] Pill

A pill weighing 4 g was prepared according to a common method by mixing 1 g of the *Aureobasidium pullulans* culture of Example 2, 1.5 g of lactose, 1 g of glycerin and 0.5 g xylitol.

[Formulation Example 10] Granule

A granule was prepared by mixing 150 g of the *Aureobasidium pullulans* culture of Example 2, 50 mg of soybean extract, 200 mg of glucose and 600 mg of starch, adding 100 mg of 30% ethanol and drying the mixture at 60° C. The prepared granule was filled in a pouch.

[Formulation Example 11] Drink

After mixing 50 mg of the *Aureobasidium pullulans* culture of Example 2, 10 g of glucose, 0.6 g of citric acid and 25 g of oligosaccharide syrup and then adding 300 mL of purified water, 200 mL of the mixture was filled in a bottle. Then, a drink was prepared by sterilizing at 130° C. for 4-5 seconds.

[Formulation Example 12] Caramel

A caramel was prepared by mixing 50 mg of the *Aureobasidium pullulans* culture of Example 2, 1.8 g of corn syrup, 0.5 g of skim milk, 0.5 g of soybean lecithin, 0.6 g of butter, 0.4 g of hydrogenated vegetable oil, 1.4 g of sugar, 0.58 g of margarine and 20 mg of table salt.

While the specific exemplary embodiments of the present disclosure have been described in detail, it will be apparent to those of ordinary skill in the art that they are merely specific exemplary embodiments and the scope of the present disclosure is not limited by them. Accordingly, it is to be understood that the substantial scope of the present disclosure is defined by the appended claims and their equivalents.

ACCESSION NUMBER

Depository authority: Korean Culture Center of Microorganisms
Accession number: KCCM12142
Date of deposit: Oct. 31, 2017
MIRCROORGANISM DEPOSIT

---

The invention claimed is:

1. A method for improving skin damage caused by fine dust, which comprises administering a composition comprising an extract of a culture of an *Aureobasidium pullulans* strain; to a subject in need of improvement of skin damage caused by fine dust
   wherein the strain is *Aureobasidium pullulans* GJW having an accession number of KCCM12142P, and wherein the extract is an ethanol fraction.

2. The method according to claim 1, wherein the strain has 18S rRNA represented by the sequence of SEQ ID NO 1.

3. The method according to claim 1, wherein the extract of a culture of the *Aureobasidium pullulans* strain; is contained in an amount of 0.001-30 wt % based on the total weight of the composition.

4. The method according to claim 1, wherein the improvement of skin damage is enhancement of skin barrier function.

5. The method according to claim 1, wherein the improvement of skin damage is moisturization of skin.

6. The method according to claim 1, wherein the improvement of skin damage is anti-aging and improvement of wrinkles.

7. The method according to claim 1, wherein the composition increases the expression of keratin 1 or claudin 4.

8. The method according to claim 1, wherein the composition is a pharmaceutical composition.

9. The method according to claim 1, wherein the composition is a cosmetic composition.

10. The method according to claim 1, wherein the composition is a food composition.

\* \* \* \* \*